US00PP16668P2

(12) United States Plant Patent
Trees

(10) Patent No.: US PP16,668 P2
(45) Date of Patent: Jun. 20, 2006

(54) ***ANGELONIA* PLANT NAMED 'BALANGLAST'**

(50) Latin Name: *Angelonia angustifolia*
Varietal Denomination: Balanglast

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 103 days.

(21) Appl. No.: 11/016,298

(22) Filed: Dec. 17, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Angelonia* plant named 'Balanglast' characterized by its pale purple/white bi-colored flowers, dark green-colored foliage, and freely flowering, upright, well-branched growth habit.

1 Drawing Sheet

Latin name of genus and species of plant claimed: *Angelonia angustifolia.*
Variety denomination: 'Balanglast'.

BACKGROUND OF THE INVENTION

The present invention relates to a new and distinct cultivar of *Angelonia* plant botanically known as *Angelonia angustifolia* and hereinafter referred to by the cultivar name 'Balanglast'.

The new cultivar was developed by the inventor in a controlled breeding program during July 2002, at Arroyo Grande, Calif. The objective of the breeding program was the development of *Angelonia* cultivars with freely branching and vigorous growth habits, unique flower colors, and continuous flowering.

The new cultivar was a naturally occurring sport of the proprietary *Angelonia angustifolia* selection identified as BFP-760, not patented, characterized by its solid dark lavender-colored flowers, medium green-colored foliage, and heavy branching habit. The new cultivar was discovered and selected by the inventor during August, 2002 at West Chicago, Ill.

Asexual reproduction of the new cultivar by terminal stem cuttings since August 2002 at West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balanglast' as a new and distinct cultivar of *Angelonia* plant:

1. Pale purple/white bi-colored flowers.
2. Dark green-colored foliage.
3. Freely flowering.
4. An upright, well-branched growth habit.

Plants of the new cultivar differ from plants of the parent primarily in flower color.

Of the *Angelonia* cultivars known to the inventor, the most similar to 'Balanglast' is the *Angelonia* cultivar AngelMist® Purple Stripe, not patented. However, in side-by-side comparisons, carried out at West Chicago, Ill., plants of the new cultivar differ from plants of 'Purple Stripe' in the following characteristics:

1. The flowers of 'Balanglast' are pale-purple/white bi-color, whereas the flowers of 'Purple Stripe' are dark-purple/white bi-color.
2. Plants of 'Balanglast' have smaller flowers than plants of 'Purple Stripe'.
3. Plants of 'Balanglast' are shorter than those of 'Purple Stripe'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balanglast'. The plants were grown in 10 cm pots for 14 weeks in a greenhouse at West Chicago, Ill.

DETAILED BOTANICAL DESCRIPTION

Figure 1:
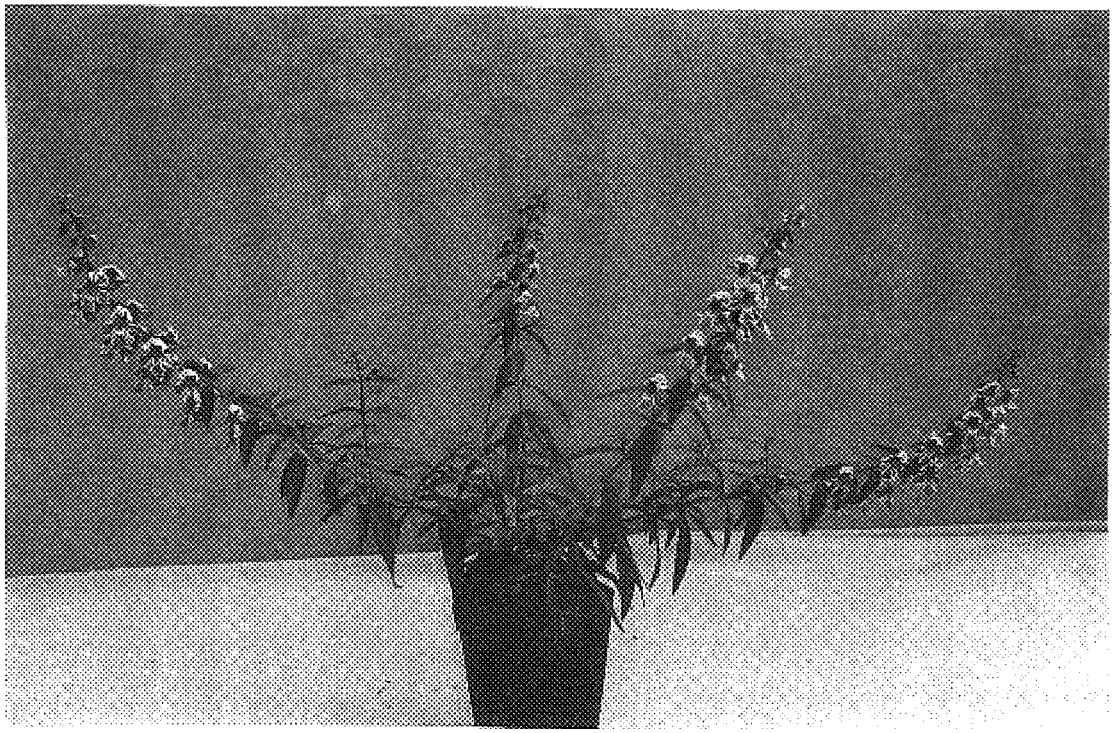
FIG. 1 illustrates a side view of the overall growth and flowering habit of 'Balanglast'.
Figure 2:
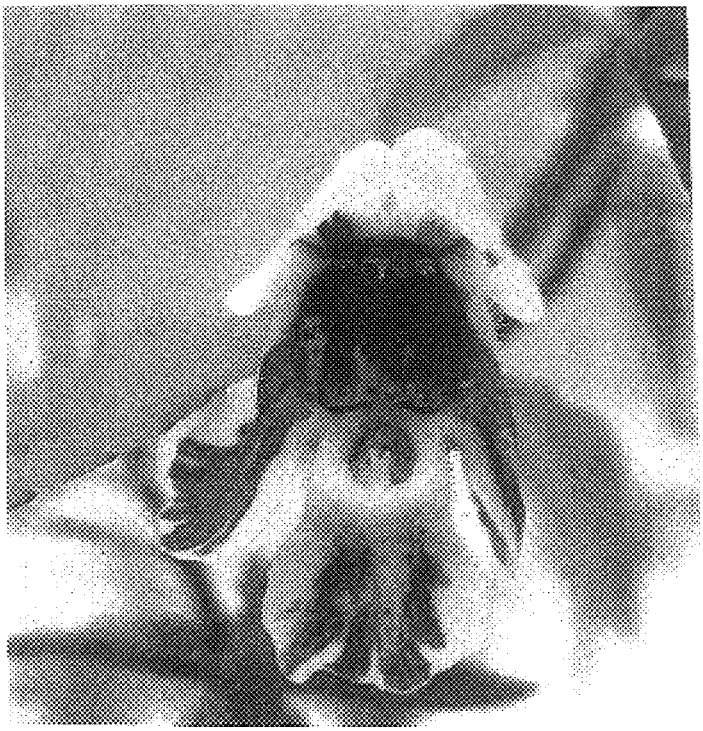
FIG. 2 illustrates a close-up view of an individual flower of 'Balanglast'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Aug. 25, 2004. The readings were taken between 1:00 and 3:00 p.m. under natural light conditions.

The following measurements and descriptions describe plants produced from cuttings taken from stock plants and grown in a double polycarbonate-covered greenhouse under conditions comparable to those used in commercial practice. The plants were grown at West Chicago, Ill. in 10 cm pots for 14 weeks while using a soilless growth medium. Greenhouse temperatures were maintained at approximately 75°–85° F. (24°–29° C.) during the day and approximately 62°–70° F. (17°–21°C.) during the night. Greenhouse light levels were maintained at approximately 6,000 to 10,000 footcandles during the day.

Botanical classification: *Angelonia angustifolia,* cultivar Balanglast.

Parentage: Naturally occurring sport of proprietary *Angelonia angustifolia* selection identified as BFP-760, not patented.

Propagation:

*Type cutting.*—Terminal stem.

*Time to initiate roots.*—Approximately 7 to 9 days.

*Time to develop roots.*—Approximately 21 to 28 days.

*Root description.*—Fine and fibrous.

*Rooting habit.*—Freely branching.

Plant description:

*Crop time.*—Approximately 6 to 7 weeks from a rooted cutting.

*Habit of growth.*—Moderately vigorous with good branching.

*Form.*—Upright and outwardly spreading.

*Size.*—Height (from soil level to top of plant plane): Approximately 29.3 cm. Diameter (area of spread): Approximately 53.1 cm.

*Main branch.*—Quantity per plant: Approximately 3. Shape: Square in cross section. Strength: Moderate. Length from soil level to branch tip: Approximately 35.7 cm. Diameter: Approximately 3.1 mm. Color: 144B. Texture: Glabrous. Internode length at middle of branch: Approximately 2.1 cm.

*Foliage.*—Quantity: Approximately 36 leaves per main branch. Fragrance: None. Type: Simple. Arrangement: Opposite. Orientation to stem: Obtuse. Shape: Narrow elliptic. Apex: Narrow acute. Base: Sessile. Margin: Dentate. Size of leaf taken from middle of branch: Length: Approximately 6.8 cm. Width: Approximately 1.5 cm. Venation pattern: Pinnate. Color of upper surface of young foliage: 146A with venation of 145C. Color of lower surface of young foliage: 146B with venation of 145C. Color of upper surface of mature foliage: Darker than 146A with venation of 145C. Color of lower surface of mature foliage: 146B with venation of 145C. Texture of upper and lower surfaces: Glabrous.

Flowering description:

*Flowering habit.*—'Balanglast' is freely flowering under outdoor growing conditions with substantially continuous blooming from spring through autumn and year round in greenhouse environment.

*Lastingness of individual bloom.*—Approximately 7 to 10 days.

*Inflorescence type/description.*—Terminal racemes. Length from base of lowest fully open flower to tip of branch: 16.3 cm. Width: 4.9 cm. Number per plant: Approximately 3 open racemes per plant. Number of fully open flowers per raceme at any one time: Approximately 13.

Flower description:

*Type/fragrance.*—Solitary, bi-labiate, self-cleaning. Flowers have a slightly sweet fragrance.

*Bud.*—Rate of opening: Generally takes 3–4 days for bud to progress from first color to fully open flower. Shape at first color: Spherical. Length: Approximately 8.3 mm. Diameter: Approximately 6.7 mm. Color: 150D.

*Flower size/aspect.*—Length: Approximately 2.4 cm. Width: Approximately 1.8 cm. Depth: Approximately 7.4 mm. Aspect: Facing outward parallel to stem.

*Petals.*—Quantity: Five per flower fused at base forming a throat, an upper lip having two petals and a lower lip having three petals.

*Upper lip.*—Petal shape: Obovate. Petal apex: Obtuse. Petal margin: Entire. Length of petals: 6.9 mm. Width of petals: 9.5 mm. Color of upper surface: Background of N155D with irregular areas of N82B and 83B. Color of lower surface: N155D at margin and N82D and 83D in center. Texture of upper surface of petals: Dense stipulate glandular at base becoming sparse at margin and apex. Gland color: Colorless, translucent. Texture of lower surface of petals: Glabrous.

*Lower lip.*—Petal shape: Obovate. Petal apex: Obtuse. Petal margin: Entire. Length of petals: 7.7 mm. Width of petals: 8.8 mm. Color of upper surface: Background of N155D with irregular areas of 83C, N82C and venation of 83B. Palate color: N155D with spots of 83A. Tooth color: 150C. Color of lower surface: N155D with irregular areas of N82D, 83D and venation of 83C. Texture of upper surface: Densely glandular at base, moderately glandular along margin and apex. Texture of lower surface: Moderately glandular. Gland color: Colorless, translucent.

*Throat.*—Length: Approximately 5 mm. Width: Approximately 8 mm. Texture: Glabrous. Color of inner and outer surfaces: 83D with spots of 83A.

*Pedicel.*—Strength: Strong. Length: Approximately 1.4 cm. Diameter: Approximately 0.4 mm. Angle to stem: Acute. Color: 144C with overlay of 187A. Texture: Glabrous.

*Calyx.*—Shape: Five pointed star. Length: Approximately 4.7 mm. Diameter: Approximately 5 mm. Sepal quantity: 5. Sepal shape: Lanceolate. Sepal apex: Acuminate. Sepal margin: Entire. Sepal length: Approximately 4.7 mm. Sepal width: Approximately 2.2 mm. Sepal color: Both surfaces: 143A with overlay of 187A. Sepal texture: Upper and lower surface: Glabrous.

*Reproductive organs.*—Androecium: Stamen quantity: Four per flower. Stamen length: Approximately 3.3 mm. Filament color: Lighter than N155A. Anther shape: Bi-lobed. Anther length: 1.8 mm. Anther color: 96C. Amount of pollen: Abundant. Pollen Color: 155D. Gynoecium: Pistil quantity: One per flower. Pistil length: 4.4 mm. Stigma length: 0.3 mm. Stigma color: Colorless, transparent. Style length: 2.6 mm. Style color: Lighter than N155A. Ovary diameter: 1.5 mm. Ovary color: 150C with overlay of 187A. Ovary texture: Glabrous.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balanglast', substantially as herein shown and described.

* * * * *